United States Patent [19]

Kou et al.

[11] Patent Number: 4,867,152

[45] Date of Patent: Sep. 19, 1989

[54] RESPIRATORY THERAPY APPARATUS WITH SELECTIVE DISPLAY OF PARAMETER SET POINTS

[75] Inventors: Abraham H. Kou, Redmond, Wash.; Robin L. Roehl, Janesville; Gerhardt P. Schroeder, Madison, both of Wis.

[73] Assignee: The BOC Group, Inc., New Providence, N.J.

[21] Appl. No.: 107,129

[22] Filed: Oct. 9, 1987

[51] Int. Cl.$^4$ ............................................ A61M 16/00
[52] U.S. Cl. .............................. 128/204.21; 128/716; 128/722; 128/723
[58] Field of Search ................. 200/DIG. 1; 307/116, 307/139; 340/365 C; 328/147, 149; 128/203.27, 200.24, 204.21, 716, 722, 725, 723; 368/69–71

[56] References Cited

U.S. PATENT DOCUMENTS

| | | | |
|---|---|---|---|
| 3,871,170 | 3/1975 | Bergey | 368/69 |
| 4,290,061 | 9/1981 | Serrano | 340/365 C |
| 4,561,002 | 12/1985 | Chiu | 340/365 C |
| 4,621,632 | 11/1986 | Bartels et al. | 128/203.27 |

Primary Examiner—Edgar S. Burr
Assistant Examiner—Aaron J. Lewis
Attorney, Agent, or Firm—Larry R. Cassett; Roger M. Rathbun

[57] ABSTRACT

Respiratory therapy apparatus is provided with setting elements such as knobs for inputting set values for various parameters. A digital display is provided for showing measured values of operational variables. The set point for each parameter is displayed on the display apparatus along with the measured values only when the knob or setting element for the particular parameter is engaged by the operator's hand.

12 Claims, 2 Drawing Sheets

RESPIRATORY THERAPY APPARATUS WITH SELECTIVE DISPLAY OF PARAMETER SET POINTS

BACKGROUND OF THE INVENTION

The present invention relates to respiratory therapy apparatus and more particularly relates to respiratory therapy apparatus having improved means for entering set values of various parameters and displaying the actual measured values of operational variables.

Respiratory therapy apparatus such as ventilators, anesthesia machines and other devices for controlling the flow of respiratory gases to and from a subject such as a medical patient may be arranged to regulate a plurality of different operational variables. Thus, a typical medical ventilator may be arranged to regulate the volume inhaled and exhaled by the patient on each breath, referred to as the "tidal volume", the breath rate or number of breaths per unit time and other variables. The ventilator typically incorporates automatic devices for monitoring each of these variables to provide measured values and controlling the apparatus based upon stored set values for various parameters. The parameters may correspond directly to the controlled variables. Thus, a stored set value of tidal volume may be used for control of the actual tidal volume used in operation of the apparatus. Alternately, a parameter may correspond indirectly to one or more operational variables. Thus, a stored set value of a parameter referred to as "inspiratory flow rate" may be used in control of variables related to the inspiratory flow rate but not having a direct, 1:1 correlation thereto. The stored set values for the parameters may include upper or lower limits for each parameter or, more typically, a so-called center point or desired value for each parameter.

The set values typically have been entered into the apparatus by actuation of movable setting elements such as a rotary knob for each parameter. Typically, each such knob has been provided with a conventional pointer and scale or other mechanical indicator directly connected to the knob. Thus, the pointer or other mechanical indicator shows the set value for the associated parameter. Typically, the measured values for the variables have been displayed on gauges, digital read outs and the like linked to the control system. The measured values thus have been displayed separately from the set values shown by mechanical indicators associated with the knobs.

These arrangements are less than optimal in many respects. It is generally difficult to obtain an accurate reading of the set value from the mechanical indicator associated with the knob. Factors such as parallax between a mechanical pointer and scale and the limited resolution available in a mechanical scale of practical size limit the accuracy with which the physician can discern the set value. Moreover, the correlation of the position of the knob and the set value entered into the apparatus is not perfect. Typically, the control system employed in the apparatus is electronic, and the knob or other movable setting element is mechanically linked to a variable electronic element such as a potentiometer. Imperfections in the mechanical linkage between the knob and the electronic element, such as shifting of a knob on the shaft of the potentiometer may alter the correlation between position of the knob and the value of the variable electronic component. Thus, imperfections in the mechanical linkage may alter the correlation between the value indicated by the mechanical pointer or indicator associated with the knob and the actual set value entered into the electronic system. Changes in the characteristic of the variable electrical element, such as changes in the resistance characteristics of a potentiometer, may have a similar effect. For all of these reasons, the mechanical indicators associated with the setting elements generally do not provide accurate indications of the set values which have been entered into the control apparatus and stored therein. Accordingly, it is difficult for the physician to detect subtle deviations of the measured values from the values expected in view of the stored set values.

Additionally, this system is inconvenient for the physician. Comparison of set and actual values may require the physician to look first at the knob and associated mechanical indicator or scale to ascertain the set value, and then at a remote display to ascertain the actual value. Where the physician desires to adjust a set value and observe the change in the actual measured values, he must continually shift his eyes back and forth from the actual value display to the mechanical indicator showing the set value. These problems are particularly serious inasmuch as respiratory therapy apparatus may be used in critical care situations where the physician must maintain close, careful surveillance of the respiratory therapy and also perform other tasks necessary to patient care. Thus, there have been significant unmet needs heretofore for improvements in respiratory therapy apparatus.

SUMMARY OF THE INVENTION

The present invention addresses those needs.

One aspect of the present invention provides medical respiratory therapy apparatus comprising means for storing set values for a plurality of therapeutic parameters, controlling the therapy based on the stored set values and monitoring operational variables to provide measured values thereof. Display means are provided. The display means normally display the measured values of the operational variables but not the set values. A setting element is associated with each parameter, and means are provided for altering the stored set value for each parameter in response to a predetermined manual setting movement of the associated setting element. For example, where potentiometers are employed to provide the set values, each set value is stored in the control system as the resistance of a particular potentiometer. A setting element in the form of a knob is associated with each potentiometer, and hence each stored set value can be changed by turning the knob associated with the appropriate potentiometer.

The apparatus according to this aspect of the present invention preferably includes means for detecting manual engagement of each setting element and actuating the display means to momentarily display the stored set value for the parameter associated with the engaged setting element along with the measured values. Where knobs are employed, the stored set value for a given parameter is displayed along with the measured values when the physician engages the setting element or knob for that parameter with his hand.

This aspect of the invention provides numerous advantages. Because the set values are not normally displayed, there is no possibility for confusion between set and actual values when the physician looks at the display. However, where the physician wishes to check the set value for any parameter, he need only engage the associated setting element and the set value for the particular parameter will be displayed Most typically, the system includes means for timing a predetermined period starting with manual engagement of the setting element and actuating the display means to display the set value of the parameter associated with the engaged setting element during this predetermined period. The apparatus may also include adjustment actuation means for actuating the display means to display the set value for each parameter in response to alteration of the set value for that parameter. Thus, if the physician merely engages the setting element or knob for a particular parameter, the set value for that parameter will be displayed for the first mentioned predetermined period during which the physician can decide whether any adjustment is necessary. If he adjusts the set value, the system will continue to display the set value in response to this adjustment, so that he may continually monitor the set value while he is adjusting it. The apparatus preferably includes means for detecting manual engagement of the setting means independently of the setting movement and, most desirably, independently of any movement of the setting element. Therefore, the set value for each parameter can be displayed without adjusting the set value. Preferably, the apparatus includes means for detecting manual engagement of a setting element by detecting a change in capacitance between an electrically conductive element juxtaposed with the setting element and the environment. Thus, the body capacitance of a physician touching a setting element triggers the display of the associated parameter, and the physician need not move the setting element or knob to obtain a parameter display.

When the setting element for a given parameter is manually engaged in this fashion, the physician's hand is already positioned on the setting element and hence the set value can be adjusted readily. Because the display means, when actuated, shows the set value for each parameter as actually stored in the control system, the inaccuracies associated with mechanical indicators and the like on the setting elements or knobs are eliminated. Thus, where the control system stores set values as potentiometer resistances, the set value which is displayed will be determined by the potentiometer resistance and not by the position of the knob or setting element. These and other objects, features and advantages of the present invention will be more readily apparent from the detailed description of the preferred embodiments set forth below taken in conjunction with the accompanying drawings.

DETAILED DESCRIPTION OF THE PREFERRED EMBODIMENTS

Figure 2:
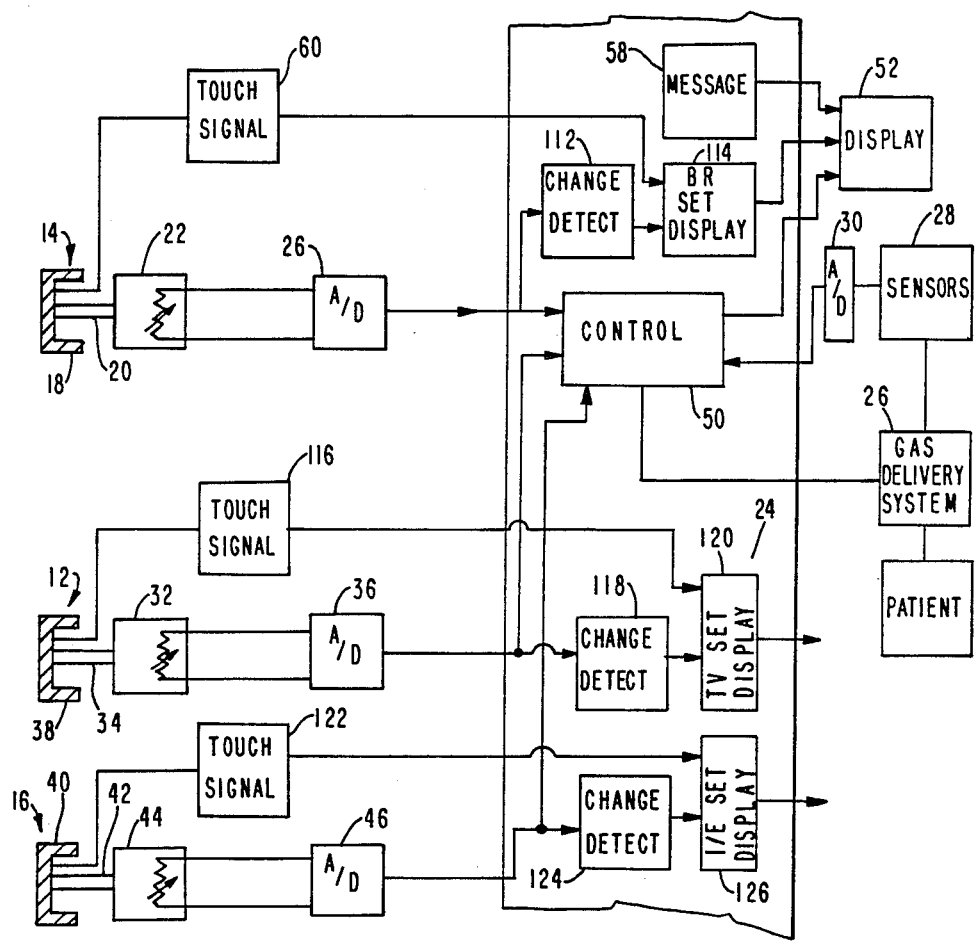
FIG. 2 is a schematic, partially block diagrammatic view showing further portions of the apparatus in FIG. 1.

Apparatus according to one embodiment of the present invention includes a housing 10 having three setting elements or knobs 12, 14, 16 rotatably mounted thereon for altering the set values of tidal volume, breath rate and inspiratory flow rate, respectively. As indicated in FIG. 2, breath rate setting element or knob 14 includes a metallic, electrically conductive portion 18 mounted at the end of a potentiometer shaft 20, connecting the knob or setting element 14 to the movable element of a potentiometer 22. Thus, the resistance of potentiometer 22 may be altered by turning knob 14 and shaft 20 about the axis of the shaft.

A microprocessor 24, of which a portion is schematically depicted in FIG. 2, is mounted within housing 10. Although various functional elements of the microprocessor are depicted separately herein for clarity of illustration, those skilled in the art will understand that typical microprocessors may use one structural element to perform a plurality of different functions The microprocessor is connected via a conventional analog to digital interface 26 to the potentiometer 22 associated with breath rate knob 14. Thus, the microprocessor can continually read the value of the resistance of potentiometer 22. The microprocessor is arranged to interpret the digitized value of the resistance of potentiometer 22, as delivered through interface 26, as the value of a set point for the breath rate. Thus, potentiometer 22 serves to store the value of the breath rate set point, and this stored value can be changed by turning knob 14.

Likewise, the tidal volume knob or setting element 12 has a metallic element 38 mounted on a potentiometer shaft 34, which in turn is connected to a potentiometer 32. Potentiometer 32 is connected through a further analog to digital interface 36 to microprocessor 24. Also, inspiratory flow rate knob 16 has a metallic element 40 mounted on a potentiometer shaft 42 which in turn is connected to a potentiometer 44, and yet another analog to digital interface 46 is connected between potentiometer 44 and microprocessor 24. Microprocessor 24 is arranged to interpret the values received through analog to digital converter 36, representing the setting of potentiometer 32, as a set value for the tidal volume, and to interpret the values received through analog to digital converter 46, representing the resistance of potentiometer 44, as a set value for the inspiratory flow rate.

The apparatus also includes a conventional gas delivery system 26 of the type normally employed in ventilators. This gas delivery system is connected to the patient in the conventional manner, so that the gas delivery system can supply respiratory gases to the patient. Conventional sensors 28 are connected to the gas delivery system for monitoring operational variables including tidal volume, breath rate and others. Sensors 28 are connected through a further conventional analog to digital interface 10 to microprocessor 24, so that the microprocessor continually receives measured values of variables via interface 30. Microprocessor 24 includes conventional control circuitry 50 for continually regulating the gas delivery system 26 based upon the digitized set values received via converters 26, 36 and 46.

Figure 1:
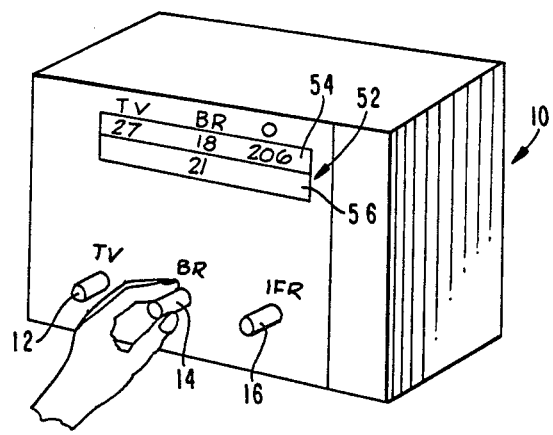
FIG. 1 is a schematic perspective view illustrating a portion of apparatus in accordance with one embodiment of the present invention.

A display unit 52 is also provided. As shown in FIG. 1, display unit 52 may be a conventional alpha-numeric, digitally driven display such as a liquid crystal display. Display unit 52 includes a first or upper array of alpha-numeric positions 54 and a lower array of positions 56. The display unit is connected via appropriate conventional driving circuitry (not shown) to microprocessor 24 so that the digitized, measured values of various parameters as supplied to the microprocessor via analog to digital converter 30, or as computed by the microprocessor from the measured values, will be continually displayed in the upper array of alphanumeric positions 54 on displaY unit 52. As shown in FIG. 1, display unit 52 is displaying actual values for tidal volume or "TV", breath rate or "BR" and another variable "O" on the upper array 54. Microprocessor 24 also includes conventional circuitry 58 for generating messages pertaining to operation of the unit such as error messages and/or instruction messages, and the message generation circuitry is also linked via conventional driving circuitry (not shown) to display unit 52 so that messages generated by the message unit 58 are normally displayed on the lower array 56 of alphanumeric positions. Thus, display unit 52 normally does not show any of the set values for the various parameters.

Figure 3:
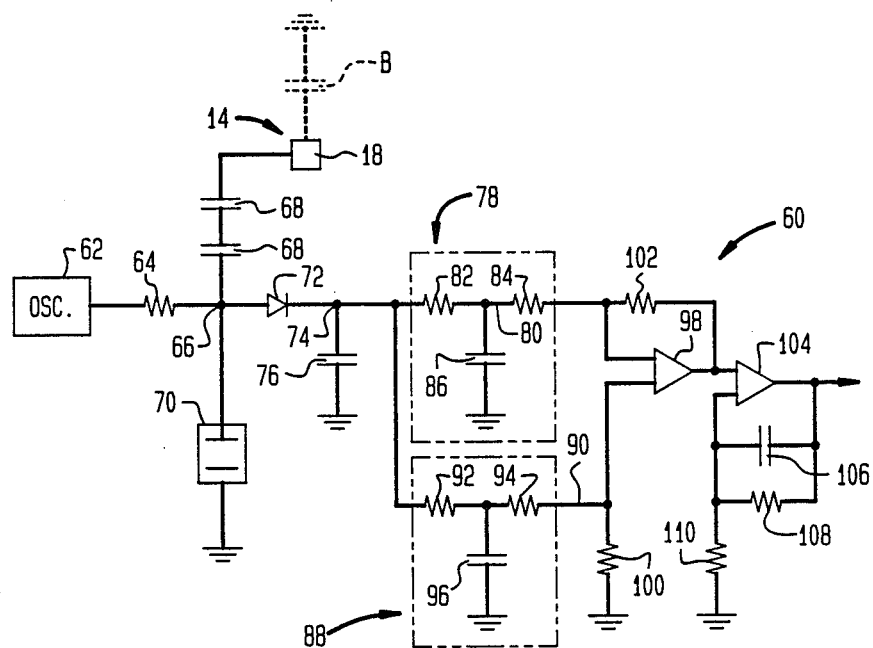
FIG. 3 is a fragmentary schematic view showing a circuit employed in the apparatus of FIGS. 1 and 2.

The metallic element 18 of setting element or knob 14 is electrically connected to touch signal generation circuit 60. As shown in FIG. 3, circuit 60 includes an oscillator 62 arranged to deliver an alternating current signal of about 500 KHz through an input impedance 64 in the form of a resistor of about 47.5 kilo-ohms to a node 66. Node 66 is capacitively connected via two capacitors 68 of 0.001 microfarads each in series to the metallic element 18 of the knob. Node 66 is also connected to one side of a neon tube 70, the other side of the neon tube being connected to the chassis ground. Additionally, node 66 is connected via a diode 72 to a further node 74 which in turn is connected to one side of a capacitor 76. Capacitor 76 has a value of about 330 pico-farads. The opposite side of capacitor 76 is connected to the digital ground of the circuit, i.e., the ground utilized for the digital components of the circuit, including microprocessor 24. Node 47 is connected to the input of a fast response filter 78 having an output node 80. Filter 78 includes an input resistor 82 of about 30.1 kilo-ohms and a capacitor 86 of about 0.0047 microfarads having one side connected to the output node 80 and the other side connected to the digital ground. Node 74 is also connected to the input side of a slow response filter 88 having an output node 90. Filter 88 includes an input resistor 92 of about 100 kilo-ohms and a capacitor 96 of about 10 microfarads having one side connected to output node 90 and the other side connected to the digital ground.

The output nodes 80 and 90 of fast response filter 78 and slow response filter 88 are connected through resistors 84 and 94 to the negative and positive inputs of a differential amplifier 98, respectively. Resistors 84 and 94 may be about 562 and about 511 kilo-ohms, respectively. The positive input is connected via a resistor 100 of about 562 kilo-ohms to the digital ground, whereas a feedback resistor 102 also of about 562 kilo-ohms is connected across the output of amplifier 98 and the negative input thereof. The output of amplifier 98 is connected to the positive input of a further amplifier 104. A feedback capacitor 106 of about 0.1 micro-farads and feedback resistor 108 of about 1 mega-ohm are connected between the output of amplifier 104 and its negative input. Also, the negative input of amplifier 104 is connected via a variable resistor 110 of about 10 kiloohms maximum value to the digital ground. A source 111 of a positive potential of about 7½ volts is connected through a further resistor 113 of about 1 mega-ohm to the negative input of amplifier 104. The output of amplifier 104 is connected through an output resistor 115 of about 1 kilo-ohm to the output node 117 of the touch signal circuit 60.

The circuit 60 will provide a square wave or pulse of the same voltage or "level" as used in the microprocessor circuit 24 at node 117 whenever knob 14 is manually engaged by the hand of a physician or other person operating the apparatus. In the absence of such engagement, the metallic element 18 may be considered as effectively isolated from ground potential. Therefore, essentially none of the AC signals delivered to node 66 through input impedance 64 will pass through capacitors 68. Accordingly, the signal at node 66 will be at a relatively constant amplitude. This relatively constant amplitude AC signal is rectified at diode 72 and delivered to capacitor 76, so that the voltage at node 74 represents a smoothed or average value of the rectified AC signal. Absent manual engagement of the knob 14 or the metallic element 18, the value of this smoothed, rectified signal at node 74 does not change appreciably or changes only at a very slow rate, well within the passbands of both filters 78 and 88. Therefore, the filtered signals appearing at the output nodes 80 and 90 of both filters will be substantially identical to one another. Substantially equal voltages will be applied at the positive and the negative inputs of amplifier 98. Therefore, the amplifier 98 will produce essentially no output.

When a physician or other person manually engages knob 14, the body capacitance (B) of the person is effectively connected between the metallic element 18 of the knob and the environment and hence between metallic element 18 and ground. As metallic element 18 is effectively coupled to ground through the bodily capacitance (B) upon such manual engagement, a significant portion of the AC signal delivered to node 66 via input impedance 64 is effectively shunted away from node 66 via capacitor 68, metallic element 18 and the bodily capacitance of the person. Therefore, the AC voltage at node 66 will suddenly drop, and the rectified, smoothed signal appearing at node 74 will likewise drop. The response characteristic or transfer function of filter 78 is fast enough that the voltage at output node 80 effectively tracks the rapidly changing voltage. However, the response characteristic or transfer function of filter 88 is slow enough that the change in output voltage at node 90 effectively lags behind the change in the smoothed, rectified voltage at node 74. Thus, while the voltage at node 74 is decreasing rapidly, the voltage at node 90 is momentarily in excess of the voltage at node 80. Amplifier 98 thus momentarily emits a significant output voltage until the voltages at node 80 and 90 again come to equilibrium. This momentary voltage pulse from amplifier 98 is applied to the input of amplifier 104, and amplifier 104 provides a squared pulse of the appropriate voltage level and duration at node 117 to serve as a signal pulse in microprocessor 24. This squared pulse constitutes a touch or manual engagement signal, and circuit 60 will emit one such engagement signal or squared pulse whenever knob 14 is touched or manually engaged by the physician or operator.

Neon tube 70 provides for electrostatic discharge protection. Voltages applied to metallic element 18 due to static electric charges carried by the physician's body, may tend to produce a sudden spike or voltage surge at node 66. However, any such surge at node 66 will cause the voltage across neon tube 70 to exceed its breakdown or arc initiation voltage, and hence will cause the neon tube to conduct, thereby shunting the surge voltage away from the remaining components of the circuit. The neon tube is selected so that it has a relatively low capacitance, preferably below about 100 pico-farads, and hence does not interfere with the aforementioned touch sensing action.

Microprocessor 24 includes change detection elements 112 which continually monitor the set value of breath rate delivered via analog to digital converter 26, i.e., which continually monitor the digitized value of the resistance of potentiometer 22. Change detection elements 112 provide a change signal whenever the digitized value from converter 26 changes. The microprocessor also includes breath rate set point display actuation elements 114. The breath rate set point display actuation elements are arranged to actuate the display 52 in a breath rate set point display mode in response to either the engagement signal from circuit 60 or the change signal from change detection elements 112. In this breath rate set point display mode, display 52 shows the actual digitized value of breath rate received by microprocessor 24 from analog to digital converter 26 on the lower array of display elements 56. As seen in FIG. 1, the numerals "21" representing a breath rate set point are displayed on lower array 56 beneath the corresponding figure "18" representing the actual or measured value of the breath rate. Breath rate set point display actuation elements 114 are arranged to time out a predetermined period following the last received manual engagement signal from circuit 60 or change signal from change detector 112, and to maintain the display 52 in the breath rate set point display mode for this predetermined period. When the predetermined period ends, the breath rate set point display elements 114 become inactive, and hence the display 52 reverts to its normal mode of operation, in which only the actual, measured values of the various parameters are shown, together with messages from unit 58. Also, breath rate set point display elements 114 are arranged to override message unit 58 while in the breath rate set point display mode, so that the lower array 56 of alpha-numeric elements is freed of messages from unit 58 and hence available to display the breath rate set point.

The metallic element 38 of the tidal volume setting element or knob 12 is connected to a touch or engagement signal generating circuit 116 similar to circuit 60, and the microprocessor includes further change detection elements 118 operative to continually check the values of the tidal volume set point delivered through analog to digital converter 36 and to provide a change signal upon any change in this value. Tidal volume set point display actuator elements 120 are also provided in the microprocessor. In a manner similar to the mode of operation of breath rate set point display actuation elements 114, the tidal volume set point display elements 120 override message unit 58 and cause display of the tidal volume set point as delivered by analog to digital converter 36 on the lower array of elements 56 of display 52 for a predetermined time after the last signal from touch circuit 116 or from change detection elements 118. A further, similar engagement detection circuit 122 and change detection elements 124 are associated with the knob or setting element 16 employed to set the inspiratory flow rate set point. However, the display actuation elements 126 associated with knob 16 do not provide display of the inspiratory flow rate setting as such. Rather, elements 126 cause display of the set value for "inspiratory/expiratory ratio", a parameter related to the inspiratory flow rate and other system parameters.

As pointed out above, the display unit 52 normally displays only the actual values of operational variables including tidal volume, breath rate and others together with any messages from unit 58. As soon as the physician or operator touches one of the knobs or setting elements 12, 14 or 16, the associated parameter will be displayed on the lower array 56 of the display unit 52. That parameter will be displayed for the aforementioned predetermined period, typically about one-and-one-half seconds. If the operator then turns the knob so as to move the knob in its predetermined setting motion and hence change the associated parameter, the set point value of the parameter will be displayed for a further predetermined period. Because the display is normally free of any indication of the set values, the physician can readily interpret the values displayed as being the actual values. However, the operator can readily obtain an indication of the set value merely by touching the appropriate knob. Whenever the set value for a particular parameter is displayed, it appears on the lower array 56 beneath the actual or measured values as displayed on the upper array 54. Thus, the operator can instantaneously compare the measured values with the set value. The set point value as displayed on unit 52 will be the digitized value actually supplied to the system through the appropriate analog to digital converter. Notably, the operator need not actuate any separate switch or button to obtain the digital display of the set value for a given parameter. Further, the same array of alpha-numeric positions 56 normally employed to display system messages and the like is used to display the set point values when required. Therefore, the display unit 52 can be economical and compact.

As will be appreciated, numerous variations and combinations of the features described above can be employed. Thus, in the system described above, the engagement signal circuits 60, 116 and 112 detect manual engagement of the various knobs or setting elements independently of any movement of these knobs. In a less preferred system, manual engagement of the knobs or setting elements could be detected only by detecting the setting movement. Thus, the engagement signal generating circuits 60, 116 and 122 could be omitted, and manual engagement of the knobs or setting elements could be detected by change detection elements 112, 118 and 124 detecting changes in the set values occasioned by the setting motion. As will be appreciated, this system would require the operator to change the set values in order to display them and hence is markedly less preferred. According to yet another variation, the knobs or setting elements may be arranged for movement other than the predetermined setting movements. The apparatus may be arranged to detect manual engagement by detecting this other movement For example, in a system employing knobs and potentiometers where a rotary movement of the knob above the axis of the potentiometer shaft constitutes the setting movement, each knob may also be arranged for longitudinal movement along the axis of the associated potentiometer shaft. The system may be provided with a switch or other element to sense longitudinal movement of each knob along the associated potentiometer shaft, and hence to detect manual engagement of the knob. In this system, manual engagement can be detected independent of the setting movement, so that the physician can obtain a display of the set values merely by pushing the knobs without turning them. However, systems such as the preferred capacitive system discussed above, which detect manual engagement independent of any movement of the knobs or setting elements are more convenient to use. The most preferred capacitive systems include metallic elements incorporated in each knob or setting element. However, it is not absolutely essential that the metallic element actually be incorporated in the knob or setting element. Rather, the metallic element need only be juxtaposed with the knob or setting element so that an operator's hand manually engaging the knob or setting element will necessarily be coupled capacitively to the metallic element. Also, systems other than capacitive systems can detect manual engagement of the knobs or setting elements independent of motion of the setting elements. For example, an optical system incorporating appropriate photodetectors can be employed to detect manual engagement of a knob or setting element. Further, although the system has been discussed above with reference to setting of three parameters, it should be readily appreciated that the system can be used in a device for setting any number of parameters.

As these and other variations and combinations of the features described above can be utilized without departing from the present invention as defined in the claims, the foregoing description of the preferred embodiments should be taken by way of illustration rather than by way of limitation of the invention as defined in the claims.

We claim:

1. Medical respiratory therapy apparatus comprising:
   (a) means for storing set values for a plurality of parameters, controlling the therapy based upon said stored set values and monitoring operational variables to provide measured values thereof;
   (b) display means for displaying values, said display means including a first group of display elements for display of said measured values and a second group of display elements for display of said set values, said display means normally displaying said measured values on said first group of display elements but not display said set values;
   (c) a setting element associated with each of said parameters;
   (d) means for altering the stored set value for each said parameter in response to a predetermined manual setting movement of the associated setting element; and
   (e) means for detecting manual engagement of each said setting element and actuating said display means in response to said manual engagement to momentarily display the stored set value for the parameter associated with the engaged setting element on said second group of display elements simultaneously with display of said measured values on said first group of display elements, said means for detecting and actuating including means for automatically timing a predetermined period starting with manual engagement of a setting element and actuating said display means to display the set value of the parameter associated with the engaged setting element during said predetermined period.

2. Apparatus as claimed in claim 1 wherein said means for detecting and actuating includes means for detecting manual engagement of each said setting element independent of occurrence of said predetermined setting movement of the setting element, whereby the set value for each said parameter can be displayed without adjusting such set value by manually engaging the associated setting element without performing said predetermined movement.

3. Apparatus as claimed in claim 2, wherein said means for detecting and actuating includes means for detecting manual engagement of each said setting element independent of any movement of the setting element.

4. Apparatus as claimed in claim 3 wherein said means for detecting and actuating includes means for detecting a change in capacitance caused by the body capacitance of an operator manually engaging a setting element.

5. Apparatus as claimed in claim 4 wherein said means for detecting a change in capacitance includes an electrically conductive element juxtaposed with each said setting element, circuit means defining a node associated with each setting element and capacitively coupled to the associated electrically conductive element and oscillator means for applying an AC signal through an input impedance to each said node, said means for detecting a change in capacitance further comprising means for monitoring signals appearing at each said node.

6. Apparatus as claimed in claim 5 wherein said means for monitoring signals appearing at each said node includes means for rectifying signals appearing at each said node and smoothing each said rectified signal to provide a rectified, smoothed signal associated with each said node, and means for detecting changes in said rectified, smoothed signals.

7. Medical respiratory therapy apparatus comprising:
   (a) means for storing set values for a plurality of parameters, controlling the therapy based upon said stored set values and monitoring operational variables to provide measured values thereof;
   (b) display means for displaying values, said display means normally displaying said measured values but not said set values;
   (c) a setting element associated with each of said parameters;
   (d) means for altering the stored set value for each said parameter in response to a predetermined manual setting movement of the associated setting element; and
   (e) means for detecting manual engagement of each said setting element and actuating said display means in response to said manual engagement to momentarily display the stored set value for the parameter associated with the engaged setting element along with said measured values,
   said means for detecting and actuating including means for detecting manual engagement of each said setting element independent of any movement of the setting element and therefore independent of occurrence of said predetermined setting movement of the setting element, whereby the set value for each said parameter can be displayed without adjusting such set value by manually engaging the associated setting element without performing said predetermined movement,
   said means for detecting and actuating including means for detecting a change in capacitance caused by the body capacitance of an operator manually engaging a setting element,
   said means for detecting a change in capacitance including an electrically conductive element juxtaposed with each said setting element, circuit means defining a node associated with each setting element and capacitively coupled to the associated electrically conductive element and oscillator means for applying an AC signal through an input impedance to each said node, said means for detecting a change in capacitance further comprising means for monitoring signals appearing at each said node, said means for monitoring signals appearing at each said node including means for rectifying signals appearing at each said node and smoothing each said rectified signal to provide a rectified, smoothed signal associated with each said node, and means for detecting changes in said rectified, smoothed signals, said means for monitoring also including a pair of filters associated with each said node, each said filter having an input and an output, said filters in each pair having different transfer functions, said means for rectifying and smoothing being connected to the inputs of said filters so that said integrated, rectified signal from each said node is provided to the inputs of both filters in the associated pair, said means for detecting a change in capacitance including means for detecting differences between signals appearing at the outputs of said filters in each said pair and providing an engagement signal upon the occurrence of such a difference.

8. Apparatus as claimed in claim 5 further comprising means for attenuating surge voltages created by electrostatic discharges applied to any of said conductive elements.

9. Apparatus as claimed in claim 5 wherein each of said setting elements includes a metallic component, and wherein the metallic component of each said setting element constitute said electrically conductive element juxtaposed with such setting element.

10. Apparatus as claimed in claim 2 further comprising adjustment actuation means for detecting a change in the set value of each said parameter and actuating said display means to display momentarily the set value of each said parameter simultaneously with said measured values in response to any such change.

11. Apparatus as claimed in claim 10 wherein said adjustment actuation means included means for automatically actuating said display means to display the set value for each said parameter simultaneously with said measured value for a predetermined time after each change in the set value for that parameter.

12. Apparatus as claimed in claim 1 further comprising means for actuating said display means to display additional messages other than said set values on said second group of display elements when said set values are not displayed.

* * * * *